United States Patent [19]

Edwards et al.

[11] Patent Number: 4,916,148
[45] Date of Patent: Apr. 10, 1990

[54] NAPHTHO(2,1-b) FURAN DERIVATIVES

[75] Inventors: Philip N. Edwards, Bramhall; Michael S. Large, Gillow Heath, both of England

[73] Assignee: Imperial Chemical Industries PLC, London, England

[21] Appl. No.: 267,319

[22] Filed: Nov. 4, 1988

[30] Foreign Application Priority Data

Nov. 12, 1987 [GB] United Kingdom ............... 8726505

[51] Int. Cl.$^4$ .................. C07D 405/10; A67K 31/41
[52] U.S. Cl. .................................. 514/383; 548/266.4
[58] Field of Search .................... 548/262; 514/383

[56] References Cited

U.S. PATENT DOCUMENTS 4,735,960 4/1988 Hirsch et al. .................... 514/383
4,757,082 7/1988 Hirsch et al. .................... 514/383

Primary Examiner—Glennon H. Hollrah
Assistant Examiner—Patricia L. Morris
Attorney, Agent, or Firm—Cushman, Darby & Cushman

[57] ABSTRACT

Naphtho[2,1-b]furan derivatives of the formula:

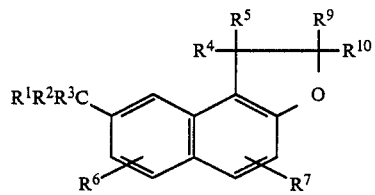

wherein $R^1$ is a 1H-1,2,4-triazol-1-yl, 4H-1,2,4-triazol-4-yl, 3-pyridyl or 5-pyrimidinyl radical or a 1H-imidazol-1-yl radical optionally substituted in the 5-position by a 1-6C alkyl or halogenoalkyl radical;

$R^2$ and $R^3$, which may be the same or different, are each a hydrogen or deuterium atom, a cyano radical, a 1-6C alkyl or halogenoalkyl radical, a phenyl radical optionally substituted by halogen, or one of $R^2$ and $R^3$ is a radical of the formula $R^1$ as defined above, and the other is hydrogen;

$R^4$ and $R^5$, which may be the same or different, are each a 1-2C alkyl, deuterioalkyl or halogenoalkyl radical;

or $R^4$ and $R^5$ together with the carbon atom to which they are attached form a 3-6C cycloalkyl radical;

$R^6$ and $R^7$, which may be the same or different, are each a hydrogen or halogen atom, an amino, carboxy, carbamoyl, cyano, 1-cyano-1-methylethyl or nitro radical, a 1-6C alkyl or halogenoalkyl radical, a mono- or di-(1-6C)alkylcarbamoyl radical, a mono- or di-(1-6C)halogenoalkylcarbamoyl radical, a group of the formula —COR$^8$, —SO$_n$R$^8$ or —OR$^8$, in which n is 0, 1 or 2 and R$^8$ is a 1-6C alkyl or halogenoalkyl radical, or a benzoyl radical optionally substituted by halogen;

one of $R^9$ and $R^{10}$ is hydrogen and the other is a hydroxy or 1-6C alkoxy radical, or $R^9$ and $R^{10}$ together form an oxo radical;

and the pharmaceutically acceptable acid addition salts thereof; processes for their manufacture; and pharmaceutical compositions containing them.

7 Claims, No Drawings

NAPHTHO(2,1-b) FURAN DERIVATIVES

This invention relates to novel naphtho[2,1-b]furan derivatives, and in particular it relates to such derivatives which are useful as inhibitors of the enzyme aromatase.

Aromatase is an enzyme which effects the aromatisation of ring A in the metabolic formation of various steroid hormones. Various cancers, for example breast cancer, are dependent for their maintenance or growth upon steroid hormones which have an aromatic ring A. Such cancers can therefore be treated by removing the source of ring A aromatised steroid hormones, for example by the combination of oophorectomy and adrenalectomy. An alternative way of obtaining the same effect is by administering a chemical compound which inhibits the aromatisation of the steroid ring A, and the compounds of this invention are useful for this purpose.

A variety of compounds possessing aromatase inhibitory activity is known, of which the most important clinically is aminoglutethimide. Aminoglutethimide, however, has the drawback that it affects other aspects of steroid metabolism, with the consequence that its use is often associated with undesirable side-effects.

Thus, according to the invention, there is provided a naphtho[2,1-b]furan derivative of the formula I shown hereafter, wherein $R^1$ is a 1H-1,2,4-triazol-1-yl, 4H-1,2,4-triazol-4-yl, 3-pyridyl or 5-pyrimidinyl radical or a 1H-imidazol-1-yl radical optionally substituted in the 5-position by a 1–6C alkyl or halogenoalkyl radical;

$R^2$ and $R^3$, which may be the same or different, are each a hydrogen or deuterium atom, a cyano radical, a 1–6C alkyl or halogenoalkyl radical, a phenyl radical optionally substituted by halogen, or one of $R^2$ and $R^3$ is a radical of the formula $R^1$ as defined above, and the other is hydrogen;

$R^4$ and $R^5$, which may be the same or different, are each a 1–2C alkyl, deuterioalkyl or halogenoalkyl radical;

or $R^4$ and $R^5$ together with the carbon atom to which they are attached form a 3–6C cycloalkyl radical;

$R^6$ and $R^7$, which may be the same or different, are each a hydrogen or halogen atom, an amino, carboxy, carbamoyl, cyano, 1-cyano-1-methylethyl or nitro radical, a 1–6C alkyl or halogenoalkyl radical, a mono- or di-(1–6C)alkylcarbamoyl radical, a mono- or di-(1–6C)halogenoalkylcarbamoyl radical, a group of the formula $-COR^8$, $-SO_nR^8$ or $-OR^8$, in which n is 0, 1 or 2 and $R^8$ is a 1–6C alkyl or halogenoalkyl radical, or a benzoyl radical optionally substituted by halogen;

one of $R^9$ and $R^{10}$ is hydrogen and the other is a hydroxy or 1–6C alkoxy radical, or $R^9$ and $R^{10}$ together form an oxo radical;

and the pharmaceutically acceptable acid addition salts thereof.

A suitable value for a 1–6C alkyl substituent in $R^1$ when it is an optionally 5-alkyl-substituted imidazole radical, or for $R^2$, $R^3$, $R^6$, $R^7$ or $R^8$, when any of them is a 1–6C alkyl radical, or for a 1–6C alkyl radical in $R^6$ or $R^7$ when either of them is a mono-or di-(1–6C)alkylcarbamoyl radical, is, for example, a methyl, ethyl, propyl, isopropyl, butyl, isobutyl, sec-butyl, tert-butyl, pentyl, isopentyl, hexyl or isohexyl radical; and a suitable value for $R^4$ or $R^5$, when either of them is a 1–6C deuterioalkyl radical is, for example, a deuteriated form of the specific alkyl radicals listed above.

A suitable value for $R^2$, $R^3$, $R^6$, $R^7$ or $R^8$, when any of them is a 1–6C halogenoalkyl radical, or for a 1–6C halogenoalkyl radical in $R^6$ or $R^7$ when either of them is a mono- or di-(1–6C)halogenoalkylcarbamoyl radical, is, for example, a chloromethyl, dichloromethyl, trichloromethyl, fluoromethyl, difluoromethyl, trifluoromethyl, 2,2,2-trichloroethyl, 2,2,2-trifluoroethyl, 1,2,2-trichloroethyl, 1,2,2-trifluoroethyl, pentafluoroethyl, 2,2,3,3,3-pentafluoropropyl, 2,2-dichloro-3,3,3-trifluoropropyl, 4,4,4-trifluorobutyl, 5,5,5-trifluoropentyl or 6,6,6-trifluorohexyl radical.

A suitable value for $R^4$ or $R^5$ is, for example, a methyl, ethyl, chloromethyl, dichloromethyl, trichloromethyl, fluoromethyl, difluoromethyl, trifluoromethyl, 2,2,2-trichloromethyl, 2,2,2-trifluoroethyl, 1,2,2-trichloroethyl, 1,2,2-trifluoroethyl or pentafluoroethyl radical.

A suitable value for the 3–6C cycloalkyl radical formed by $R^4$, $R^5$ and the carbon atom to which they are attached is a cyclopropyl, cyclobutyl, cyclopentyl or cyclohexyl radical.

A suitable value for $R^9$ or $R^{10}$, when either of them is a 1–6C alkoxy radical, is, for example, a methoxy, ethoxy, propoxy, isopropoxy, butoxy, pentyloxy or hexyloxy radical.

A preferred value for $R^1$ is a 1H-1,2,4-triazol-1-yl, 4H-1,2,4-triazol-1-yl, 1H-imidazol-1-yl or 5-methyl-1H-imidazol-1-yl radical, and of these the 1H-1,2,4-triazol-1-yl radical is particularly preferred.

A preferred value for $R^2$ is a hydrogen atom, and preferred values for $R^3$ are hydrogen, cyano, methyl, trifluoromethyl, 4-chlorophenyl and 1H-1,2,4-triazol-1-yl radicals, particularly hydrogen, 4-chlorophenyl and 1H-1,2,4-triazol-1-yl.

Preferred values for $R^4$ and $R^5$ are methyl or ethyl radicals, and it is particularly preferred that $R^4$ and $R^5$ are both methyl radicals.

A preferred value for a cycloalkyl ring formed by $R^4$, $R^5$ and the carbon atom to which they are attached is a cyclopentyl radical.

Preferred values for $R^6$ and $R^7$ are hydrogen, cyano, bromo, 4-chlorobenzoyl, nitro, amino, carbamoyl, carboxy, dimethylcarbamoyl, 2,2,2-trifluoroethylcarbamoyl and mesyl, and particularly hydrogen, cyano, bromo, 4-chlorobenzoyl, nitro, carbamoyl, 2,2,2-trifluoroethylcarbamoyl and mesyl. Preferably, one of $R^6$ and $R^7$ is hydrogen, and preferably the one other than hydrogen is in the 5- or 7-position, of which the 7-position is particularly preferred.

Preferably, $R^9$ and $R^{10}$ together form an oxo radical, or one is hydrogen and the other is a hydroxy or ethoxy radical.

Suitable pharmaceutically acceptable acid addition salts are, for example, hydrochlorides, hydrobromides, sulphates, nitrates, phosphates and toluene-p-sulphonates.

It is to be understood that either or both of the carbon atom bearing the substituents $R^1$, $R^2$ and $R^3$, the carbon atom bearing the substituents $R^4$ and $R^5$, and the carbon atom bearing the substituents $R^9$ and $R^{10}$ may be asymmetrically substituted, so that the compounds of the invention may exist in racemic or optically active forms. It is common general knowledge in the art how such optically active forms may be synthesised and their respective aromatase inhibitory properties determined.

Particularly preferred compounds of the invention are 1,1-dimethyl-8-(1H-1,2,4-triazol-1-ylmethyl)-2(1H)-naphtho[2,1-b]furanone (Example 1) 1,2-dihydro-1,1-dimethyl-2-oxo-8-(1H-1,2,4-triazol-1-ylmethyl)naphtho[2,1-b]furan-7-carbonitrile (Example 4), 1,2-dihydro-1,1-dimethyl-2-oxo-8-(1H-1,2,4-triazol-1-ylmethyl)-naphtho[2,1-b]furan-7-carboxamide (Example 16), and 1,2-dihydro-1,1-dimethyl-2-oxo-8-[di(1H-1,2,4-triazol-1-yl)methyl]naphtho[2,1-b]furan-7-carbonitrile (Example 21).

The compounds of the invention may be manufactured by processes known per se for the manufacture of analogous compounds. Thus, according to a further feature of this invention, there is provided a process for the manufacture of a compound of the formula I which comprises (a) the reaction of a naphtho[2,1-b]furan compound of the formula II, wherein Y is a known leaving group, and Y' is a radical of the formula Y or a radical of the formula $R^2$, which may be isolated as such or may be formed in situ from the corresponding 8-(1-hydroxyalkyl) compound, with a heterocyclic compound of the formula $R^1H$, or with a silyl or a reactive metal derivative thereof, or with a protected derivative thereof wherein a nitrogen atom which is not to be involved in the reaction with the compound of the formula I is protected by a known nitrogen protecting group, whereafter the said protecting group is removed; or (b) for those compounds of the invention wherein one of $R^9$ and $R^{10}$ is an alkoxy radical, the reaction of a halogen compound of the formula III with a 1-6C alkanol; whereafter if desired:

(i) for those compounds wherein $R^6$ or $R^7$ is a nitro radical, a compound of the invention, wherein $R^6$ and $R^7$ are both other than a nitro radical, is nitrated, (ii) for those compounds wherein $R^6$ or $R^7$ is an amino radical, the reduction of a corresponding compound of the invention wherein $R^6$ or $R^7$ is a nitro radical;

(iii) for those compounds wherein $R^6$ or $R^7$ is a carbamoyl radical, the hydrolysis of a corresponding compound of the invention wherein $R^6$ or $R^7$ is a cyano radical;

(iv) for those compounds wherein $R^6$ or $R^7$ is a carboxy radical, the hydrolysis of a corresponding compound of the invention wherein $R^6$ or $R^7$ is a cyano radical;

(v) for those compounds wherein $R^6$ or $R^7$ is a carbamoyl, mono-or di(1-6C)alkylcarbamoyl or mono- or di-(1-6C)halogenoalkyl radical, the reaction of a corresponding compound of the invention wherein $R^6$ or $R^7$ is a carboxy radical, or a reactive derivative thereof, such as an acid halide, acid anhydride, mixed anhydride or reactive ester, with an amino derivative of the formula $R^{11}R^{12}NH$, wherein $R^{11}$ and $R^{12}$, which may be the same or different, are each hydrogen or a 1-6C alkyl or halogenoalkyl radical;

(vi) for those compounds wherein one of $R^9$ and $R^{10}$ is hydrogen and the other is a hydroxy radical, the reduction of a corresponding compound of the invention wherein $R^9$ and $R^{10}$ together form an oxo radical.

In the process (a) of the invention, a suitable value for the known leaving group Y is, for example, a halogen atom such as a chlorine or bromine atom, or sulphonyloxy radical such as a mesyloxy or tosyloxy radical.

A suitable metal derivative of the heterocyclic compound of the formula $R^1H$ is an alkali metal derivative, such as sodium 1H-1,2,4-triazole or 3-pyridyl-lithium.

A suitable silyl derivative of the heterocyclic compound of the formula $R^1H$ is, for example, 1-trimethylsilyl-1H-1,2,4-triazole.

A suitable known nitrogen protecting group for a nitrogen atom in $R^6$ which is intended not to be involved in the reaction with the compound of the formula I is, for example, an amino or trityl radical. Such an amino protecting group can be removed by reaction with nitrous acid, and such a trityl protecting group can be readily removed by acid treatment.

The compound of the formula II, wherein $R^2$ and $R^3$ are both hydrogen atoms, and $R^4$ and $R^5$ are each a 1-2C alkyl radical, which is used as the starting material in the above process (a), may be obtained by reacting the appropriate 7-methyl-2-naphthol (IV) with thioglycolic acid, $HS.CH_2.COOH$, to form the corresponding 2-hydroxy-7-methyl-1-naphthylacetic acid (V), which is then lactonised by heating to form the 8-methylnaphtho[2,1-b]furan-2-one derivative (VI). This derivative (VI) is then alkylated, for example with an alkyl iodide in the presence of a base such as sodium hydride, to form the alkylated lactone (VII), which is than halogenated, for example with N-bromosuccinimide to form the required starting material (II).

Alternatively, and especially if either $R^6$ or $R^7$ is an alkyl or halogenoalkyl radical, a corresponding 7-alkoxycarbonyl-2-naphthol (VIII) is reduced, for example with lithium borohydride, to form an alcohol (IX), which is then protected, using a known hydroxy-protecting group, for example trimethylsilyl, to give the protected compound (X). The compound (X) is then reacted with thioglycolic acid to give the naphthylacetic acid (XI), which is then cyclised by heating to form the lactone (XII). This derivative is then alkylated, for example with an alkyl iodide in the presence of a base such as sodium hydride, to give the compound (XIII). The hydroxy protecting group is then removed to give the corresponding alcohol (XIV), which in turn is halogenated to form a starting material of the formula (II) wherein Y is a halogen atom, or reacted with an appropriate sulphonyl chloride to form a starting material of the formula (II) wherein Y is a sulphonyloxy leaving group, for example a tosyloxy or mesyloxy group.

The compound of the formula (II) wherein $R^2$ and $R^3$ are both deuterium atoms, which may be used as starting material in the process of the invention, may be obtained similarly, but using lithium aluminium deuteride in place of lithium borohydride as the reducing agent for the compound (VIII).

The 7-methyl-2-naphthol (IV) and 7-alkoxycarbonyl-2-naphthol derivatives (VIII) are either known compounds or are obtainable from known compounds by standard known methods of aromatic organic chemistry.

In particular, however, 7-alkoxycarbonyl-2-naphthyl compounds bearing an additional substituent $R^6$ or $R^7$ which is a 1-cyano-1-methylethyl radical may be obtained by reaction of the corresponding compound wherein $R^6$ or $R^7$ is a methyl radical with N-bromosuccinimide to form the corresponding bromomethyl compound, which is then treated with potassium cyanide to give the corresponding cyanomethyl compound, which in turn is alkylated with methyl iodide in the presence of a base to give the required 1-cyano-1-methylethyl substituted compound.

Starting materials of the formula II for the above process, wherein $R^4$ and $R^5$ together with the carbon atom to which they are attached form a 3-6C cycloalkyl radical may be obtained similarly by alkylating the lactone intermediate (VI) with the appropriate alkylene dihalide in the presence of a base, for example sodium hydride.

The starting material of the formula II, wherein one of $R^2$ and $R^3$ is other than a hydrogen atom, which is used in the above process (a), may be obtained by oxidising a compound of the formula II wherein Y is a bromine atom, for example with silver tetrafluoroborate in dimethylsulphoxide, to the formyl derivative XV, which is then reacted with a Grignard reagent of the formula $R^2MgBr$.

Alternatively, particularly for compounds of the formula II wherein $R^2$ is a halogenoalkyl radical, 7-methoxy-1-tetralone (XVI) is acylated with an ester $R^2CO_2Et$ to a β-diketone (XVII) which is reduced with sodium borohydride to the corresponding diol (XVIII). The diol is dehydrated with potassium hydrogen sulphate to the unsaturated alcohol (XIX) which is aromatised with 2,3-dichloro-5,6-dicyanobenzoquinone to the corresponding naphthalene derivative. Demethylation with boron tribromide to the naphthol (XX) followed by reaction with thioglycolic acid in the presence of base and thermal lactonisation gives the naphtho[2,1-b]furan derivative (XXI). The side chain hydroxy group is protected by reaction with tert-butyldimethylsilyl chloride to give a hydroxy-protected derivative which is alkylated to XXII with an iodoalkane, $R^4I$, and the protecting silyl ether is removed with tetrabutylammonium fluoride to give the required compound of the formula II.

The compound of the formula III, which is used as the starting material in the above process (b), may be obtained from a corresponding compound of the invention wherein one of $R^9$ and $R^{10}$ is hydrogen and the other is a hydroxy radical, by reaction thereof with a halogenating agent such as thionyl chloride.

As indicated above, the compounds of the invention of the formula I are useful as aromatase inhibitors. Aromatase inhibition may be demonstrated by the following tests:

DEMONSTRATION OF ACTIVITY IN VITRO

Aromatase inhibitory activity was measured using the enzyme present in the microsomal fraction of human term placenta, as described by Ryan, J. Biol, Chem., 234, 268, (1959). Enzyme activity was determined by measuring the amount of tritiated water released from 0.5 micromolar (1β,2β- $^3H$)testosterone after 20 minutes incubation at 37°. The method used was essentially that described by Thomson and Siiteri, J. Biol. Chem. 249, 5364, (1974), except that testosterone was used in place of androstenedione. Test compounds were dissolved in dimethylsulphoxide (DMSO) then diluted as appropriate to achieve final concentrations of 2, 0.2 or 0.02 μg/ml. The reaction was started by the addition of 50 μl of microsome suspension to 50 μl of a solution containing substrate (testosterone) and cofactors (NADPH glucose-6-phosphate and glucose-6-phosphate dehydrogenase) and either DMSO alone or a DMSO solution of test compound. Each concentration of test compound was tested in triplicate. The reaction was stopped by the addition of 200 μl of a 5% (w/v) suspension of charcoal in a 0.5% (w/v) solution of Dextran T70 in water. After 1 hour the charcoal was precipitated by centrifugation and 150 μl of supernatant removed, and the amount of tritiated water present was determined using a liquid scintillation counter. The number of counts in supernatant from incubations containing test compound, expressed as a percentage of the counts in supernatant from incubations containing only DMSO, was taken as the degree of enzyme inhibition achieved by the test compound.

DEMONSTRATION OF ACTIVITY IN VIVO

Activity in vivo was demonstrated in terms of ovulation inhibition in female rats. Daily vaginal smears were taken from rats housed under controlled lighting (lights on 06.00 hr to 20.00 hr) and those having a vaginal smear pattern consistent with 4-day ovarian cycles were selected. To these rats a single dose of test compound was given either at 16.00 hr on Day 2 of the cycle or at 12.00 hr on Day 3 of the cycle. The rats were then killed in the morning following Day 4 of the cycle—approximately 64 hours after Day 2 treatments or approximately 46 hours after Day 3 treatments—and the presence or absence of eggs in the fallopian tubes determined. The presence of eggs indicates that the rats have ovulated. Without treatment more than 95% of rats with 4-day ovarian cycles are found to have ovulated at the time of the post-mortem examination. At an effective dose, aromatase inhibitors prevent ovulation, i.e. no eggs are found in the fallopian tubes.

In the above tests, the compounds of formula I are active at less than 2 μg/ml (in vitro), and/or 10 mg/kg (in vivo) and the preferred compounds of the formula I are active at below 0.02 μg/ml (in vitro) and/or 0.5 mg/kg (in vivo), and no indication of any toxicity has been seen at these doses.

Thus, according to a further feature of the invention there is provided a pharmaceutical or veterinary composition which comprises an effective amount of a compound of the formula I together with a pharmaceutically or veterinarily acceptable diluent or carrier.

The composition of the invention may be in a conventional pharmaceutical form suitable for oral administration, for example a tablet, a capsule, an emulsion or an aqueous or oily solution or suspension. The composition may contain conventional pharmaceutical excipients, and may be manufactured by conventional pharmaceutical techniques.

Preferred pharmaceutical or veterinary compositions of the invention are tablets and capsules containing from 0.1 to 100 mg, preferably 1 to 25 mg, of a compound of the invention.

The invention is illustrated but not limited by the following Examples. Melting points are given in degrees Celsius and are uncorrected. Flash chromatography was carried out on kieselguhr (Merck's Kieselgel 60H - trade mark).

EXAMPLE 1

A solution of 8-bromomethyl-1,1-dimethyl-2(1H)-naphtho[2,1-b]furanone in acetonitrile (5 ml), was treated with 1,2,4-triazole (1.4 g) and the mixture was heated under reflux for 18 h. The solution was evaporated to dryness under reduced pressure and the residue was partitioned between 1N aqueous sodium hydrogen carbonate and ethyl acetate. The ethyl acetate extract was separated, dried and evaporated to dryness, and the residue was purified by flash chromatography. Elution with methanol:chloroform, 1:49 v/v, gave 1,1-dimethyl-8-(1H-1,2,4-triazol-1-ylmethyl)-2-(1H)-naphtho[2,1-b]furanone, m.p. 136°-137° after recrystallisation from a mixture of ethyl acetate and cyclohexane.

Further elution with methanol:chloroform (1:24 v/v) gave 1,1-dimethyl-8-(4H-1,2,4-triazol-4-ylmethyl)-2(1H)-naphtho[2,1-b]furanone, m.p. 256°–257° after recrystallisation from ethanol.

The 1,1,8-trimethyl-2(1H)-naphtho[2,1-b]furanone used as the starting material in the above process may be obtained as follows:

A mixture of 7-methylnaphth-2-ol (5 g), thioglycolic acid (3 g), sodium hydroxide (2 g) and ethylene glycol (10 ml) was stirred at 145° under an atmosphere of argon for 20 h. The mixture was cooled, water (100 ml) was added, and the mixture was heated at 90° for 2 h. The mixture was then washed with ethyl acetate and the aqueous phase was separated, acidified with concentrated hydrochloric acid, and extracted twice with ethyl acetate. The ethyl acetate extracts were combined, dried and evaporated to dryness under reduced pressure, and the residue was triturated with toluene. The insoluble solid thus produced was filtered off, washed with toluene and dried to give 2-hydroxy-7-methyl-1-naphthylacetic acid, m.p. 138°–140°.

The 2-hydroxy-7-methyl-1-naphthylacetic acid thus obtained was heated at 150° for 1 h and cooled, and the product was crystallised from ethyl acetate to give 8-methyl-2(1H)-naphtho[2,1-b]furanone, m.p. 170°–171°.

An ice-cooled solution of the naphtho[2,1-b]furanone thus obtained (1.5 g) and iodomethane (3 g) in tetrahydrofuran (20 ml) was stirred under an atmosphere of argon while sodium hydride (0.75 g of a 50% dispersion in oil) was added in portions over 20 minutes. The mixture was stirred for 1 h at room temperature, treated with aqueous ammonium chloride solution, then extracted twice with diethyl ether. The ether extracts were combined, dried and evaporated to dryness under reduced pressure, and the residue was purified by flash chromatography. Elution with ethyl acetate:pentane, 1:19 v/v, gave 1,1,8-trimethyl-2(1H)naphtho[2,1-b]furanone, m.p. 88°–89°, after recrystallisation from ethanol.

A mixture of 1,1,8-trimethyl-2(1H)-naphtho[2,1-b]furanone (1.13 g), N-bromosuccinimide (0.98 g), benzoyl peroxide (0.05 g) and carbon tetrachloride (30 ml) was heated under reflux for 1.5 h and filtered, and the filtrate was evaporated to dryness under reduced pressure, to give 8-bromomethyl-1,1-dimethyl-2[1H]-naphtho[2,1-b]furanone, which was used without further purification.

EXAMPLE 2

The process described in Example 1 was repeated, using imidazole in place of 1,2,4-triazole, to give 1,1-dimethyl-8-(1H-imidazol-1-ylmethyl)-2(1H)-naphtho[2,1-b]furanone, m.p. 135°–136° after recrystallisation from a mixture of acetone and cyclohexane.

EXAMPLE 3

A mixture of 8-bromomethyl-1,1-dimethyl-2(1H)-naphtho[2,1-b]furanone (0.46 g), 4-methyl-1-tritylimidazole (0.49 g) and acetonitrile (2 ml) was heated under reflux for 18 h, then evaporated to dryness. The residue was treated with glacial acetic acid (4 ml) and water (1 ml), and the mixture was heated at 90° for 0.5 h. The mixture was diluted with water (20 ml) and washed with diethyl ether. The aqueous phase was separated, basified with potassium hydrogen carbonate and extracted twice with ethyl acetate. The extracts were combined, dried and evaporated to dryness, and the residue was purified by flash chromatography, eluting with methanol:ethyl acetate, 1:99 v/v, to give 1,1-dimethyl-8-(5-methylimidazol-1-ylmethyl)-2(1H)-naphtho[2,1-b]furanone, m.p. 88°–91°.

The 4-methyl-1-tritylimidazole used in the above process was prepared as follows:

A mixture of trityl chloride (17 g), triethylamine (8.5 ml), 4-methylimidazole (5 g) and toluene (40 ml) was stirred at 80° for 4 h and filtered, and the solid material was washed with toluene. It was then partitioned between water and chloroform, and the chloroform solution was separated, dried and combined with the dried toluene filtrate. The combined organic solutions were evaporated to dryness under reduced pressure, and the residue was triturated with diethyl ether to give 4-methyl-1-tritylimidazole, m.p. 214°–216°.

EXAMPLE 4

A solution of 8-bromomethyl-1,2-dihydro-1,1-dimethyl-2-oxonaphtho[2,1-b]furan-7-carbonitrile in N,N-dimethylformamide (3 ml) was treated with sodium 1,2,4-triazole (0.18 g) and the mixture was stirred at room temperature for 4 h, then treated with water (20 ml). The mixture was extracted twice with ethyl acetate and the combined extracts were dried and evaporated to dryness under reduced pressure. The residue was purified by flash chromatography using methanol:ethyl acetate, 1:99 v/v, as eluant to give 1,2-dihydro-1,1-dimethyl-2-oxo-8-(1H-1,2,4-triazol-1-ylmethyl)naphtho(2,1-b)-furan-7-carbonitrile, m.p. 198°–198° after recrystallisation from a mixture of ethyl acetate and cyclohexane.

The starting material used in the above process was obtained as follows:

A mixture of 1,1,8-trimethyl-2-(1H)-naphtho[2,1-b]furanone (3.85)g, trifluoracetic acid (25 ml) and hexamine (3.5 g) was stirred under reflux for 18 h. The bulk of the trifluoroacetic acid was evaporated under reduced pressure and the residue was treated with water and heated at 90° for 10 minutes. The mixture was neutralised with potassium hydrogen carbonate and extracted twice with chloroform. The combined extracts were dried and evaporated to dryness, and the residue was recrystallised from ethyl acetate to give 7-formyl-1,1,8-trimethyl-2(1H)-naphtho[2,1-b]furanone (2.2 g), m.p. 193°–195° C.

A mixture of the above aldehyde (4.3 g), hydroxylamine hydrochoride (1.74 g), sodium acetate (2.05 g), ethanol (30 ml) and water (10 ml) was stirred under reflux for 2 h. The mixture was cooled, diluted with water and exracted with chloroform, and the chloroform extract was dried and eaporated to dryness under reduced pressure.

An ice-cooled mixture of the residue, dioxan (20 ml) and pyridine (10 ml) was stirred while trifluoracetic anhydride (5.25 g) was added dropwise over 10 minutes, and the resulting solution was stirred at room temperature for 18 h. The mixture was treated with water (100 ml) and extracted with chloroform, and the extract was washed successively with 2N aqueous hydrochloric acid and water, then dried and evaporated to dryness. The residue was boiled with ethyl acetate (20 ml) and the insoluble solid was collected to give 1,2-dihydro-1,1,8-trimethyl-2-oxonaphtho[2,1-b]furan-7-carbonitrile; m.p. 215°–217° after recrystallisation from a mixture of ethanol and chloroform.

A mixture of 1,2-dihydro-1,1,8-trimethyl-2-oxonaphtho[2,1-b]furan-7-carbonitrile, (0.25 g), N-bromosuccinimide (0.2 g), benzoyl peroxide (0.01 g) and carbon tetrachloride (40 ml) was stirred under reflux for 24 h. The reaction mixture was cooled, washed with water, dried and evaporated to dryness under reduced pressure, to give the required starting material, 8-bromomethyl-1,2-dihydro-1,1-dimethyl-2-oxonaphtho[2,1-b]furan-7-carbonitrile, which was used without further purification.

EXAMPLES 5-10

The process described in Example 4 was repeated, using the appropriate 8-bromomethyl-2(1H)-naphtho[2,1-b]furanone starting material, to give the following compounds:

| Example | R³/R⁴ | R⁶ | R⁷ | M.p. |
|---------|-------|----|----|------|
| 5 | Me/Me | Br | H | 163-5 |
| 6 | Me/Me | CN | Br | 185-6 |
| 7 | Et/Et | H | H | 135-6 |
| 8 | Et/Et | CN | H | 149-151 |
| 9 | —(CH₂)₄— | H | H | 133-5 |
| 10 | Me/Me | 4-chlorobenzoyl | H | * |

*N.m.r. in deuteriochloroform: δ 8.45(1H,s); 8.0(1H,s); 7.98(1H,s); 7.82(1H,d); 7.72-7.78(3H,m); 7.44-7.52(3H,m); 5.82(2H,s); 1.72(6H,s).

The starting material for Example 5 was obtained as follows:

A solution of bromine (0.05 ml) in acetic acid (2 ml) was added over 5 minutes to a solution of 2-hydroxy-7-methyl-1-naphthylacetic acid (0.21 g) in acetic acid (5 ml). The solid which precipitated was collected and washed with acetic acid to give 7-bromo-8-methyl-2(1H)-naphtho[2,1-b]furanone, m.p. 238°-240°.

A solution of the above furanone (0.35 g) in N-methylpyrrolidinone (2 ml) was added to a stirred mixture of iodomethane (0.39 ml), sodium hydride (80% dispersion in mineral oil, 0.11 g) and N-methylpyrrolidinone (3 ml) at 0° under an atomsphere of argon. The mixture was stirred a further 0.5 h and then acidified with glacial acetic acid. The mixture was treated with water (50 ml) and extracted with ethyl acetate, and the extract was dried and evaporated to dryness under reduced pressure. The residue was purified by flash chromatography using dichloromethane:petroleum ether (b.p. 60°-80°), 1:2 v/v, as eluant to give 7-bromo-1,1,8-trimethyl-2(1H)-naphtho[2,1-b]furanone, m.p. 187°-189°, which was brominated by the process described in the last part of Example 4.

The starting material for Example 6 was obtained as follows:

A mixture of 1,2-dihydro-1,1,8-trimethyl-2-oxonaphtho[2,1-b]furan-7-carbonitrile (0.25 g), silver trifluoromethanesulphonate (0.34 g) and dichloromethane (10 ml) was stirred in the dark, while a solution of bromine (0.19 g) in dichloromethane (2 ml) was added over 10 minutes. The mixture was stirred a further 0.5 h, then treated with aqueous sodium hydrogen carbonate solution, and the resulting mixture was filtered through a pad of diatomaceous earth ("Celite" -trade mark). The organic phase was separated, dried and evaporated to dryness under reduced pressure. The residue was purified by flash chromatography, using chloroform:pentane, 1:1 v/v, as eluant, to give 9-bromo-1,2-dihydro-1,1,8-trimethyl-2-oxonaphtho[2,1-b]furan-7-carbonitrile, m.p. 235°-237° after recrystallisation from a mixture of ethyl acetate and petroleum ether (b.p. 60°-80°), which was brominated by the process described in the last part of Example 4.

The starting material for Example 7, 1,1-diethyl-8-methyl-2(1H)-naphtho(2,1-b)furanone, (m.p. 78°-80°), was made by the process described above for the manufacture of the starting material for Example 5, but using iodoethane in place of iodomethane.

The starting material for Example 8, 1,2-dihydro-1,1-diethyl-8-methyl-2-oxonaphtho(2,1-b)furan-7-carbonitrile, (m.p. 137°-140°), was made by the process described above for the manufacture of the starting material for Example 4, using 1,1-diethyl-8-methyl-2(1H)-naphtho[2,1-b]furanone in place of 1,1-trimethyl-2(1H)-naphtho[2,1-b]furanone.

The starting material (m.p. 126°-128°) for Example 9 was obtained by the process used for the manufacture of the starting material for Example 5, but using 1,4-dibromobutane in place of iodomethane.

The starting material for Example 10 was obtained as follows:

A 2M solution of 4-chlorophenyl magnesium bromide in diethyl ether (1.1 ml) was added over 5 minutes to a stirred solution of 7-formyl-1,1,8-trimethyl-2-(1H)-naphtho(2,1-b)furanone in tetrahydrofuran (5 ml) at −20°. The mixture was allowed to warm to room temperature and was then treated with 1M hydrochloric acid (20 ml). The mixture was extracted twice with ethyl acetate and the combined extracts were dried and evaporated to dryness under reduced pressure.

A solution of the residue in dichloromethane (15 ml) was treated with pyridinium chlorochromate (0.65 g) and the mixture was stirred at room temperature for 1 h. The mixture was purified by flash chromatography eluting with dichloromethane, to give 7-(4-chlorobenzoyl)-1,1,8-trimethyl-2(1H)-naphtho(2,1-b)furanone m.p. 130°-132°, which was brominated by the process described in the last part of Example 4.

EXAMPLE 11

A mixture of 8-(α,4-dichlorobenzyl)-1,1-dimethyl-2(1H)-naphtho[2,1-b]furanone, 1,2,4-triazole (0.3 g), potassium carbonate (0.3 g) and acetonitrile (5 ml) was heated under reflux for 18 h. The mixture was treated with water (20 ml) and extracted with ethyl acetate. The ethyl acetate extract was dried and then evaporated to dryness, and the residue was purified by flash chromatography eluting with methanol:chloroform, 1:99 v/v, to give 8-[4-chloro-α-(1H-1,2,4-triazol-1-yl)benzyl]-2(1H)-naphtho[2,1-b]furanone. Nmr in deuteriochloroform: δ8.12(2H,s); 7.94(1H,d); 7.36-7.46(4H,m); 7.15-7.25(3H,m); 6.92(1H,s); 1.62(3H,s); 1.60(3H,s).

The 8-(α,4-dichlorobenzyl) compound used as starting material in the above process was obtained as follows:

A mixture of 1,18-trimethyl-2(1H)-naphtho[2,1-b]furanone (0.68 g), N-bromosuccinimide (0.64 g), benzoyl peroxide (0.02 g) and carbon tetrachloride (15 ml) was stirred under reflux for 3 h, and filtered, and the filtrate was evaporated to dryness under reduced pressure.

A mixture of the residue, dimethylsulphoxide (3 ml) and silver tetrafluoroborate (0.78 g) was stirred at room temperature under an atomsphere of argon for 2 h.

Triethylamine (0.5 ml) was added, the mixture was stirred for a further 0.5 h and diluted with water, and the resulting mixture was extracted twice with ethyl acetate. The combined exracts were dried and evaporated to dryness and the residue was purified by flash chromatography using dichloromethane as eluant, to give 8-formyl-1,1-dimethyl-2(1H)-naphtho[2,1-b]furanone, m.p. 135°–137°.

A 1.1M solution of 4-chlorophenyl magnesium bromide in diethyl ether (1 ml) was added over 5 minutes to a solution of 8-formyl-1,1-dimethyl-2(1H)-naphtho[2,1-b]furanone (0.24 g) in tetrahydrofuran (5 ml) at 0°. The solution was kept at 0° for a further 15 minutes and then treated with aqueous ammonium chloride solution, and the mixture was extracted with ethyl acetate. The extract was dried and then evaporated to dryness under reduced pressure.

A solution of the residue in dichloromethane (5 ml) was treated with thionyl chloride (0.2 ml) and the solution stirred at 0° while adding pyridine (0.1 ml) over 5 minutes. The mixture was stirred a further 15 minutes and then evaporated to dryness under reduced pressure. The residue was partitioned between water and ethyl acetate, and the ethyl acetate was dried and evaporated to dryness under reduced pressure, to give the required starting material, 8-($\alpha$,4-dichlorobenzyl)-1,1-dimethyl-2(1H)-naphtho[2,1-b]furanone, which was used without further purification.

EXAMPLE 12

The process described in Example 11 was repeated, using methyl magnesium chloride instead of 4-chlorophenylmagnesium bromide, to give 1,1-dimethyl-8-[1-(1H-1,2,4-triazol-1-yl)ethyl]-2(1H)-naphtho(2,1-b)furanone. Nmr in deuteriochloroform: $\delta$8.2(1H,s); 8.04(1H,s); 7.92(1H,d); 7.82(1H,d); 7.65(1H,d); 7.38(1H,d); 7.32(1H,dd); 5.75(1H,q); 2.05(3H,d); 1.74(3H,s); 1.68(3H,s).

EXAMPLES 13–14

Nitric acid (72% by weight, 0.045 ml) was added dropwise to a stirred, ice-cooled mixture of 1,1-dimethyl-8-(1H-1,2,4-triazol-1-ylmethyl)-2(1H)-naphtho[2,1-b]furanone (0.44 g) and acetic anhydride (6 ml). The mixture was stirred at room temperature for 18 h, then added to a stirred mixture of aqueous sodium hydrogen carbonate solution and ethyl acetate. The organic phase was separated, dried and evaporated to dryness under reduced pressure, and the residue was purified by flash chromatography. Elution with ethyl acetate:pentane, 3:1 v/v, gave 1,1-dimethyl-7-nitro-8-(1H-1,2,4-triazol-1-ylmethyl)-2(1H)-naphtho[2,1-b]furanone, m.p. 183°–185° after recrystallisation from ethyl acetate. (Example 13).

Further elution with ethyl acetate gave 1,1-dimethyl-5-nitro-8-(1H-1,2,4-triazol-1-ylmethyl)-2(1H)-naphtho[2,1-b]furanone, m.p. 150°–152° after recrystallisation from ethyl acetate. (Example 14).

EXAMPLE 15

A mixture of 1,1-dimethyl-7-nitro-8-(1H-1,2,4-triazol-1-ylmethyl)-2(1H)-naphtho[2,1-b]furanone (0.035 g), glacial acetic acid (2 ml) and 10% palladium-on-carbon (0.01 g) was stirred under an atmosphere of hydrogen at room temperature and atmospheric pressure for 2 h. The mixture was filtered, the filtrate was evaporated to dryness under reduced pressure, and the residue was partitioned between ethyl acetate and equeous sodium hydrogen carbonate solution. The ethyl acetate phase was dried and evaporated to dryness under reduced pressure, and the residue was purified by flash chromatography using methanol:ethyl acetate, 1:99 v/v. as eluant, to give 7-amino-1,1-dimethyl-8-(1H-1,2,4-triazol-1-ylmethyl)-2(1H)-naphtho[2,1-b]furanone, m.p. 160°–163°.

EXAMPLE 16

A solution of 1,2-dihydro-1,1-dimethyl-2-oxo-8-(1H-1,2,4-triazol-1-ylmethyl)naphtho[2,1-b]furan-7-carbonitrile, (0.35 g) and concentrated sulphuric acid (2 ml) was kept at room temperature for 18 h. The mixture was treated with crushed ice and neutralised with concentrated aqueous ammonia, and the mixture was extracted twice with ethyl acetate. The combined extracts were dried and evaporated to dryness under reduced pressure, and the residue was purified by flash chromatography using methanol:dichloromethane, 1:14 v/v, as eluant, to give 1,2-dihydro-1,1-dimethyl-2-oxo-8-(1H-1,2,4-triazol-1-ylmethyl)naphtho[2,1-b]furan-7-carboxamide, m.p. 231°–232° after recrystallisation from a mixture of methanol and ethyl acetate.

EXAMPLE 17

A mixture of 1,2-dihydro-1,1-dimethyl-2-oxo-8-(1H-1,2,4-triazol-1-ylmethyl)naphtho[2,1-b]furan-7-carbonitrile, (0.48 g) and 10N sulphuric acid (5 ml) was stirred under reflux for 24 h. The mixture was treated with dimethyl sulphoxide (2 ml), heated under reflux for a further 18 h, cooled and basified with 5N sodium hydroxide solution. The mixture was washed with ethyl acetate, the aqueous phase was acidified with glacial acetic acid, and the precipitate was collected to give 1,2-dihydro-1,1-dimethyl-2-oxo-8-(1H-1,2,4-triazol-1-ylmethyl)naphtho[2,1-b]furan-7-carboxylic acid, m.p. 262°–265°.

EXAMPLE 18

A mixture of 1,2-dihydro-1,1-dimethyl-2-oxo-8-(1H-1,2,4-triazol-1-ylmethyl)naphtho[2,1-b]furan-7-carbonyl chloride, dimethylamine hydrochloride (0.25 g) and dichloromethane (2 ml) was stirred at 0° and treated with triethylamine (1 ml), and stirring was continued for 0.5 h. The mixture was treated with water (10 ml) and extracted twice with chloroform, and the combined extracts were dried and evaporated to dryness under reduced pressure. The residue was purified by flash chromatography, using methanol:dichloromethane, 1:50 v/v, as eluant, to give 1,2-dihydro-1,1,N,N-tetramethyl-2-oxo-8-(1H-1,2,4-triazol-1-ylmethyl)naphtho[2,1-b]furan-7-carboxamide, m.p. 172°–173°.

The carbonyl chloride starting material used in the above process was obtained as follows:

A mixture of 1,2-dihydro-1,1-dimethyl-2-oxo-8-(1H-1,2,4-triazol-1-ylmethyl)naphtho[2,1-b]furan-7-carboxylic acid (0.1 g), dichloromethane (2 ml), thionyl chloride (0.033 ml) and N,N-dimethylformamide (0.01 ml) was heated under reflux for 1.5 h, then evaporated to dryness under reduced pressure, to give the required carbonyl chloride starting material, which was used without further purification.

EXAMPLE 19

The process described in Example 18 was repeated, using 2,2,2-trifluoroethylamine hydrochloride in place of dimethylamine hydrochloride, to give 1,2-dihydro-1,1-dimethyl-2-oxo-8-(1H-1,2,4-triazol-1-ylmethyl)-N-

(2,2,2-trifluoroethyl)naphtho[2,1-b]furan-7-carboxamide, m.p. 200°–201°.

EXAMPLE 20

A solution of 8-dibromomethyl-1,1-dimethyl-2-(1H)-naphtho[2,1-b]furanone in N,N-dimethylformamide (5 ml) was treated with sodium 1,2,4-triazole (0.54 g) and the mixture was stirred at 50° for 18 h. The mixture was treated with water (50 ml) and extracted twice with ethyl acetate, and the combined extracts were dried and evaporated to dryness under reduced pressure. The residue was purified by flash chromatography using methanol:dichloromethane, 1:49 v/v, as eluant to give 1,1-dimethyl-8-[di(1H-1,2,4-triazol-1-yl)methyl]-2(1H)-naphtho[2,1-b]furanone, m.p. 193°–195° (dihydrochloride salt).

The 8-dibromomethyl compound used as the starting material in the above process was made as follows:

A mixture of 1,1,8-trimethyl-2-(1H)-naphtho[2,1-b]furanone (0.34 g), N-bromosuccinimide (0.54 g), benzoyl peroxide (0.01 g) and carbon tetrachloride (20 ml) was stirred under reflux for 4 h, cooled and filtered, and the filtrate was evaporated to dryness under reduced pressure, to give the required 8-dibromomethyl starting material, which was used without further purification.

EXAMPLE 21

The process described in Example 20 was repeated, using 8-dibromomethyl-1,2-dihydro-1,1-dimethyl-2-oxonaphtho[2,1-b]furan-7-carbonitrile in place of 8-dibromomethyl-1,1-dimethyl-2(1H)-naphtho[2,1-b]furanone, to give 1,2-dihydro-1,1-dimethyl-2-oxo-8-[di(1H-1,2,4-triazol-1-yl)methyl]naphtho[2,1-b]furan-7-carbonitrile, m.p. 240°–242°.

EXAMPLE 22

The process described in Example 1 was repeated, using 2-bromo-2-(1,1-dimethyl-2-oxonaphtho[2,1-b]furan-8-yl)acetonitrile in place of 8-bromomethyl-1,1-dimethyl-2(1H)-naphtho[2,1-b]furanone as starting material, to give 2-(1,2-dihydro-1,1-dimethyl-2-oxo-naphtho[2,1-b]furan-8-yl)-2-(1H-1,2,4-triazol-1-yl)acetonitrile, m.p. 196°–198° after recrystallisation from a mixture of ethyl acetate and cyclohexane.

The starting material used in the above process may be obtained as follows:

A mixture of crude 8-bromomethyl-1,1-dimethyl-2(1H)-naphtho[2,1-b]furanone (prepared as described in Example 1–0.4 g), dichloromethane (5 ml) and tetraethylammonium cyanide (0.31 g) was kept at room temperature for 18 h. The solution was washed with water, dried and evaporated to dryness, and the residue was purified by flash chromatography, using ethyl acetate: pentane, 1:4 v/v as eluant, to give the required starting material m.p. 159°–160°, which was brominated with N-bromosuccinimide by the process described in Example 1.

EXAMPLE 23

The process described in Example 1 was repeated, using 2-bromo-2-(7-cyano-1,2-dihydro-1,1-dimethyl-2-oxonaphtho[2,1-b]furan-8-yl)acetonitrile as starting material, to give 1-(7-cyano-1,2-dihydro-1,1-dimethyl-2-oxonaphtho[2,1-b]furan-8-yl)-1-(1H-1,2,4-triazol-1-yl)acetonitrile, m.p. 203°–205°. The 2-bromo-2-(7-cyano-1,2-dihydro-1,1-dimethyl-2-oxonaphtho[2,1-b]-8-yl)acetonitrile (m.p. 226°–228°), used as the starting material in the above process, was obtained by a similar process to that described for the starting material in Example 22.

EXAMPLE 24

A mixture of 1,2-dihydro-1,1-dimethyl-2-oxo-8-(1H-1,2,4-triazol-1-ylmethyl)naphtho[2,1-b]furan-7-carbonitrile (0.07 g), ethanol (2 ml) and sodium borohydride (0.05 g) was stirred at room temperature for 18 h. Water (10 ml) was added, and the mixture was extracted with chloroform, and the extract was dried and evaporated to dryness under reduced pressure. The residue was recrystallised from ethyl acetate to give 1,2-dihydro-2-hydroxy-1,1-dimethyl-8-(1H-1,2,4-triazol-1-ylmethyl)-naphtho[2,1-b]furan-7-carbonitrile, m.p. 219°–222°.

EXAMPLE 25

The process described in Example 24 was repeated, using 1,2-dihydro-1,1-dimethyl-2-oxo-8-(1H-1,2,4-triazol-1-ylmethyl) naphtho[2,1-b]furan-7-carboxamide as starting material, to give 1,2-dihydro-2-hydroxy-1,1-dimethyl-8-(1H-1,2,4-triazol-1-ylmethyl)naphtho[2,1-b]furan-7-carboxamide, recrystallised from ethyl acetate, m.p. 223°–5°.

EXAMPLE 26

A solution of 2-chloro-1,2-dihydro-1,1-dimethyl-8-(1H-1,2,4-triazol-1-ylmethyl)naphtho[2,1-b]furan-7-carbonitrile in ethanol (5 ml) was treated with triethylamine (0.06 ml), and the mixture was kept at room temperature for 3 h and then evaporated to dryness under reduced pressure. The residue was purified by flash chromatography, using methanol:dichloromethane, 1:200 v/v as eluant, to give 2-ethoxy-1,2-dihydro-1,1-dimethyl-8-(1H-1,2,4-triazol-1-ylmethyl)naphtho[2,1-b]-furan-7-carbonitrile, m.p. 128°–129°.

The 2-chloro compound used as the starting material in the above process was obtained as follows:

A mixture of 1,2-dihydro-2-hydroxy-1,1-dimethyl-8-(1H-1,2,4-triazol-1-ylmethyl)-naphtho[2,1-b]furan-7-carbonitrile (0.16 g), thionyl chloride (0.055 ml) and dichloromethane (3 ml) was heated under reflux for 3 h and then evaporated to dryness, to give the required 2-chloro starting material, which was used in the above process without further purification.

EXAMPLE 27

A solution of 8-bromomethyl-4,7-dimesyl-1,1-dimethyl-2(1H)-naphtho[2,1-b]furanone in acetonitrile (5 ml) was treated with 1,2,4-triazole (0.2 g) and potassium carbonate (0.14 g), and the mixture was stirred under reflux for 18 h. The mixture was diluted with water, neutralised with glacial acetic acid and extracted with ethyl acetate, and the ethyl acetate extract was dried and evaporated to dryness under reduced pressure. The residue was purified by flash chromatography, using methanol:ethyl acetate, 1:99 v/v as eluant, to give 4,7-dimesyl-1,1-dimethyl-8-(1H-1,2,4-triazol-1-ylmethyl)-2(1H)-naphtho[2,1-b]furanone, m.p. 263°–264° after recrystallisation from ethyl acetate.

The starting material for the above process was obtained as follows:

A mixture of 1,1,8-trimethyl-2-(1H)-naphtho[2,1-b]furanone (0.68 g) and chlorosulphonic acid (5 ml) was stirred at 60° for 1 h. The cooled mixture was added to crushed ice and the precipitate was collected and washed with water.

The crude bis(sulphonylchloride) so obtained was added to a stirred solution of sodium sulphite (1.6 g) in water (5 ml) at 70° and the mixture was stirred at 70° for 4 h. The cooled mixture was basified to pH9 with 2N sodium hydroxide solution and the mixture was treated with dioxan (5 ml) and methyl iodide (3 ml). The mixture was stirred at room temperature for 72 h, treated with ethyl acetate (10 ml) and the insoluble solid collected to give the dimesyl compound, m.p. 325°–327°.

A mixture of the dimesyl compound (0.19 g), N-bromosuccinimide (0.11 g), benzoyl peroxide (0.005 g) and 1,2-dichloroethane (5 ml) was stirred under reflux for 18 h. The mixture was evaporated to dryness under reduced pressure, the residue was stirred with water (10 ml), and the insoluble solid was collected, to give the required 8-bromomethyl starting material, which was used without further purification.

EXAMPLE 28

The process described in Example 27 was repeated, using 8-bromomethyl-7-mesyl-1,1-dimethyl-2(1H)-naphtho[2,1-b]furanone as the starting material, to give 7-mesyl-1,1-dimethyl-8-(1H-1,2,4-triazol-1-ylmethyl)-2(1H)-naphtho[2,1-furanone, crystallised from ethanol, m.p. 255°–256°.

The 8-bromomethyl-7-mesyl-1,1-dimethyl-2(1H)-naphtho[2,1-b]furanone, (m.p. 210°–211°, crystallised from ethyl acetatecyclohexane), used as the starting material in the above process, was prepared in a similar manner to that described for the starting material for Example 27, except that the chlorosulphonation was carried out at 0° for 0.25 h.

EXAMPLE 29

A solution of 1,1-dimethyl-8-(2,2,2-trifluoro-1-tosyloxyethyl)-2(1H)-naphtho[2,1-b]furanone and 1,2,4-triazole (0.5 g) in tetrahydrothiophen-1,1-dioxide (1 ml) was heated at 140° for 18 h. The mixture was treated with water (20 ml) and extracted twice with diethyl ether, and the combined ether extracts were dried and evaporated to dryness under reduced pressure. The residue was purified by flash chromatography, using ethyl acetate: pentane, 1:1 v/v, as eluant, to give 1,1-dimethyl-8-[1-(1H-1,2,4-triazol-1-yl)-2,2,2-trifluoroethyl]-2(1H)-naphtho[2,1-b]furanone. Nmr in deuteriochloroform: δ 8.35(1H,s); 8.15(1H,d); 8.09(1H,s); 7.98(1H,d); 7.87(1H,d); 7.51(1H,dd); 7.46(1H,d); 6.14(1H,q); 1.78(3H,s); 1.75(3H,s).

The starting material used in the above process was obtained as follows:

A mixture of 7-methoxy-1-tetralone (7.8 g), ethyl trifluoroacetate (6 ml), sodium hydride (80% dispersion in mineral oil, 1.8 g) and tetrahydrofuran (75 ml) was stirred under reflux for 2 h under an atmosphere of argon. The cooled reaction mixture was treated with 20% acetic acid solution (250 ml) and the mixture was extracted twice with ethyl acetate. The extracts were combined, dried and evaporated to dryness under reduced pressure, and the residue was recrystallised from ethanol to give 7-methoxy-2-(2,2,2-trifluoracetyl)-1-tetralone, m.p. 89°–90°.

A mixture of the above tetralone (10 g), sodium borohydride (5 g) and ethanol (30 ml) was heated under reflux for 2 h. The cooled mixture was stirred and acidified by dropwise addition of 2N aqueous hydrochloric acid then diluted with water (200 ml). The mixture was extracted twice with ethyl acetate and the combined extracts were dried and evaporated to dryness under reduced pressure.

The residue was mixed with powdered potassium hydrogen sulphate (10 g) and the mixture was stirred at 160° for 4 h, then cooled to room temperature and treated with water (50 ml). The mixture was extracted with ethyl acetate, and the extracts was dried and evaporated to dryness. The residue was purified by flash chromatography, using ethyl acetate: pentane, 1:19 v/v, as eluant, to give 1-(7-methoxy-3,4-dihydronaphth-2-yl)-2,2,2-trifluoroethanol m.p. 66°–68°.

A solution of this compound (2.8 g) in dioxan (50 ml) at 80° was stirred, 2,3-dichloro-5,6-dicyano-1,4-benzoquinone (2.75 g) was added, and the mixture was stirred at 80° for 0.5 h. The mixture was cooled to room temperature and filtered, and the filtrate was evaporated to dryness under reduced pressure. The residue was purified by flash chromatography, using ethyl acetate:petroleum ether, 1:3 v/v, (bp. 60°–80°) as eluant, to give 1-(7-methoxynaphth-2-yl)-2,2,2-trifluoroethanol m.p. 85°–87° C.

The solution of this compound (0.51 g) in dichloromethane (10 ml) was stirred at −70° under an atmosphere of argon while a 1M solution of boron tribromide in dichloromethane (2.5 ml) was added. The mixture was warmed to room temperature, stirred at room temperature for 5 h, and then treated with 10% aqueous sodium hydrogen carbonate solution (50 ml). The mixture was extracted twice with diethyl ether and the combined extracts were dried and evaporated to dryness under reduced pressure. The residue was purified by flash chromatography, using ethyl acetate:petroleum ether (bp. 60°–80°), 1:3 v/v, as eluant, to give 7-(1-hydroxy-2,2,2-trifluoroethyl)naphth-2-ol m.p. 174°–175°, after recrystallisation from a mixture of ethyl acetate and cyclohexane.

A mixture of the above naphthol (0.24 g), thioglycolic acid (0.1 g), sodium hydroxide (0.06 g) and ethylene glycol was stirred under argon at 150° for 18 h. The cooled mixture was treated with 2N aqueous hydrochloric acid (10 ml) and the mixture was extracted with ethyl acetate. The extract was dried and evaporated to dryness under reduced pressure and the residue was heated at 140° for 0.5 h. The product was purified by flash chromatography, using chloroform as eluant, to give 8-(1-hydroxy-2,2,2-trifluoroethyl)-2-(1H)-naphtho[2,1-b]furanone, m.p. 208°–209° C.

A mixture of this furanone (0.26 g), tetrahydrofuran (5 ml), tert-butyl-dimethylsilyl chloride (0.3 g) and imidazole (0.14 g) was stirred at room temperature for 18 h and then evaporated to dryness. The residue was partitioned between petroleum ether (bp 60°–80°) and water, and the petroleum ether phase was dried and evaporated to dryness.

The residue was purified by flash chromatography, using dichloromethane:petroleum ether (bp. 60°–80°) 2:3 v/v, as eluant, to give 8-(1-tert-butyl-dimethylsilyloxy-2,2,2-trifluorethyl)-2(1H)-naphtho[2,1-b]furanone.

A solution of this compound (0.2 g) and iodomethane (0.28 g) in N-methylpyrrolidinone (2 ml) was stirred at 0° while sodium hydride (80% dispersion in mineral oil, 0.03 g) was added. The mixture was stirred for 2 h and then treated with 1N aqueous hydrochloric acid (20 ml). The mixture was extracted with diethyl ether, and the extract was dried and evaporated to dryness under reduced pressure. A solution of the residue in tetrahydrofuran (2 ml) was treated with a 1M solution of tetrabutylammonium fluoride in tetrahydrofuran (1 ml) and the solution was stirred at room temperature for 1 h, then treated with water (10 ml). The mixture was extracted with ethyl acetate, and the extract was dried and evaporated to dryness. The residue was purified by flash chromatography, using ethyl acetate:petroleum ether (bp. 60°–80°), 1:6 v/v. as eluant, to give 8-(1-hydroxy-2,2,2-trifluroroethyl)-1,1-dimethyl-2(1H)-naptho[2,1-b]furanone m.p. 142°–145°.

A mixture of 8-(1-hydroxy-2,2,2-trifluoroethyl)-1,1-dimethyl-2(1H)-naphtho[2,1-b]furanone (0.04 g), pyridine (0.5 ml) and tosyl chloride (0.04 g) was stirred at room temperature for 18 h and then heated at 50° for 6 h. The mixture was cooled to room temperature, treated with water (10 ml) and the mixture was stirred at room temperature for 5 minutes and acidified with 2N aqueous hydrochloric acid. The mixture was extracted with ethyl acetate and the extract was dried and evaporated to dryness under reduced pressure to give the required starting material, 1,1-dimethyl-8-(2,2,2-trifluoro-1-tosyloxyethyl)-2(1H)-naphtho[2,1-b]furanone, which was used without further purification.

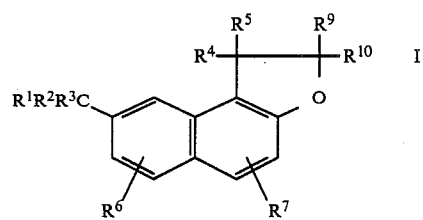

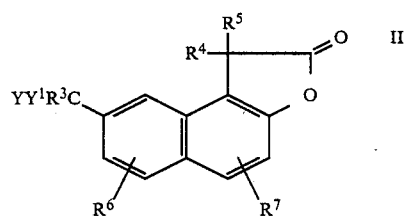

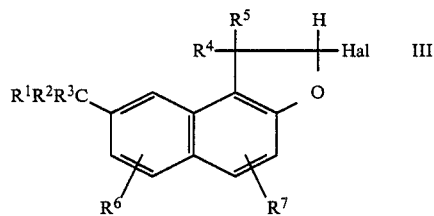

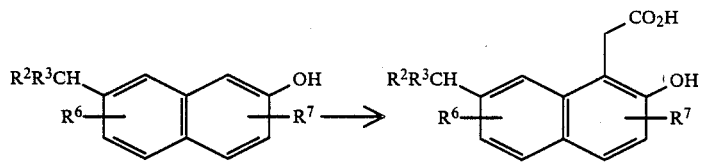

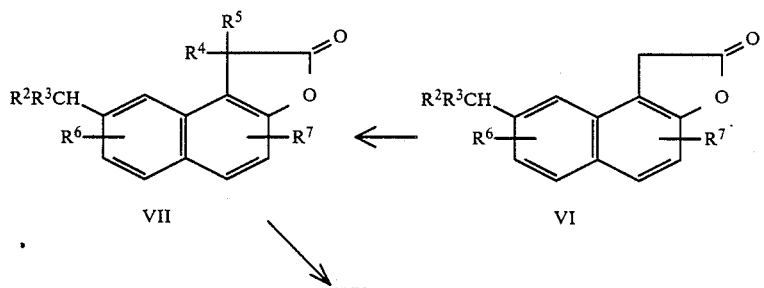

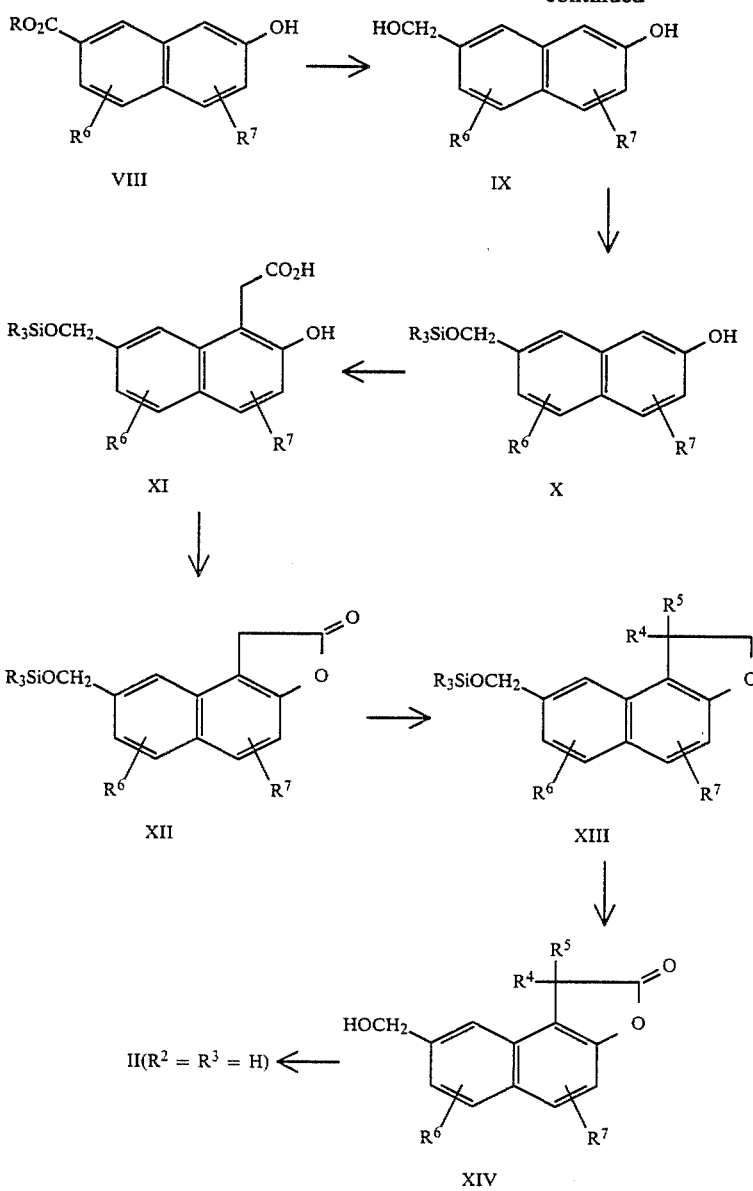
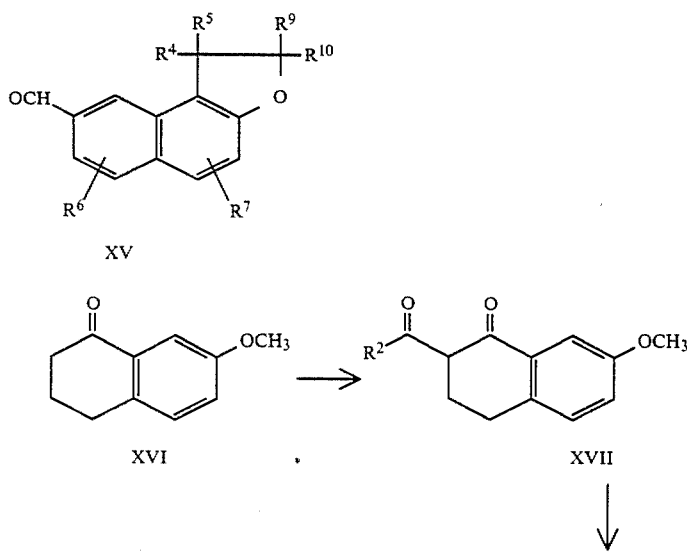

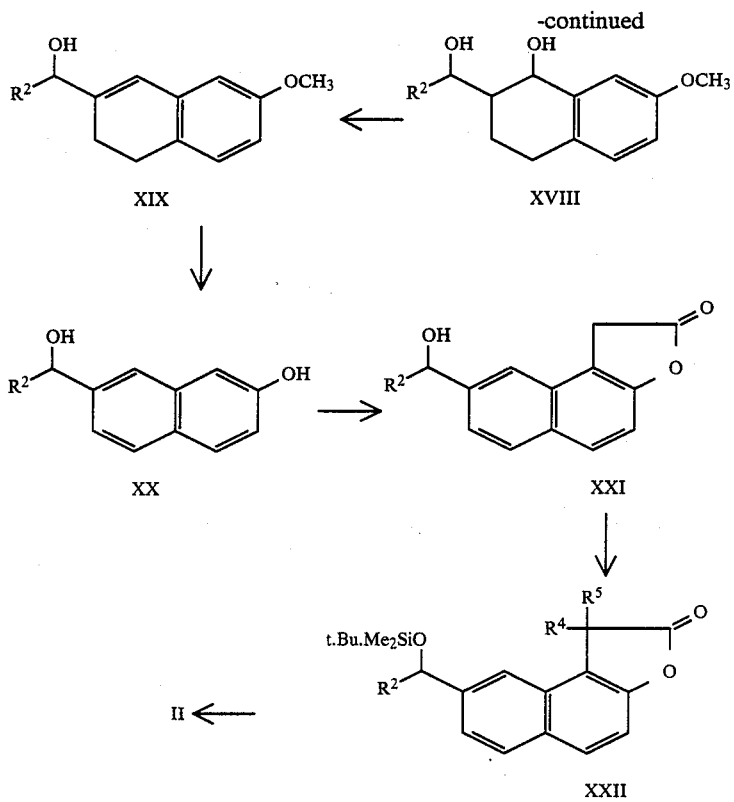

We claim:
1. A naphtho[2,1-b]furan derivative of the formula:

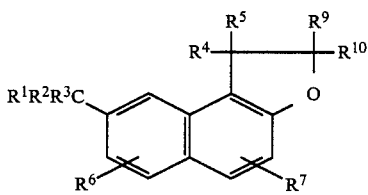

wherein
R$^1$ is a 1H-1,2,4-triazol-1-yl or 4H-1,2,4-triazol-4-yl, radical optionally substituted in the 5-position by a 1-6C alkyl or halogenoalkyl radical;

R$^2$ and R$^3$, which may be the same or different, are each a hydrogen or deuterium atom, a cyano radical, a 1-6C alkyl or halogenoalkyl radical, a phenyl radical optionally substituted by halogen, or one of R$^2$ and R$^3$ is a radical of the formula R$^1$ as defined above, and the other is hydrogen;

R$^4$ and R$^5$, which may be the same or different, are each a 1-2C alkyl, deuterioalkyl or halogenoalkyl radical;

R$^6$ and R$^7$, which may be the same or different, are each a hydrogen or halogen atom, an amino, carboxy, carbamoyl, cyano, 1-cyano-1-methylethyl or nitro radical, a 1-6C alkyl or halogenoalkyl radical, a mono- or di-(1-6C)alkylcarbamoyl radical, a mono- or di-(1-6C)halogenoalkylcarbamoyl radical, a group of the formula —COR$^8$, —SO$_n$R$^8$ or —OR$^8$, in which n is 0, 1 or 2 and R$^8$ is a 1-6C alkyl or halogenoalkyl radical, or a benzoyl radical optionally substituted by halogen;

one of R$^9$ and R$^{10}$ is hydrogen and the other is a hydroxy or 1-6C alkoxy radical, or R$^9$ and R$^{10}$ together form an oxo radical; and the pharmaceutically acceptable acid addition salts thereof.

2. A naphtho[2,1-b]furan derivatives as claimed in claim 1 wherein R$^1$ has the meaning stated in claim 1; R$^2$ and R$^3$, which may be the same or different are each a hydrogen or deuterium atom, a cyano radical, a methyl, ethyl, propyl, isopropyl, butyl, isobutyl, sec-butyl, tert-butyl, pentyl, isopentyl, hexyl or isohexyl, chloromethyl, dichlormethyl, trichlormethyl, fluoromethyl, difluoromethyl, trifluormethyl, 2,2,2-trichloroethyl, 2,2,2-trifluoroethyl, 1,2,2-trichloroethyl, 1,2,2-trifluoroethyl, pentafluoroethyl, 2,2,3,3,3-pentafluoropropyl, 2,2-dichloro-3,3,3-trifluoropropyl, 4,4,4-trifluorobutyl, 5,5,5-trifluoropentyl or 6,6,6-trifluorohexyl radical, or a phenyl radical optionally substituted by halogen, or one of R$^2$ and R$^3$ is a radical of the formula R$^1$ as defined above and the other is hydrogen; R$^4$ and R$^5$ are each a methyl or ethyl radical or a deuteriated form thereof, or a chloromethyl, dichloromethyl, trichloromethyl, fluoromethyl, difluoromethyl, trifluoromethyl, 2,2,2-trichloromethyl, 2,2,2-trifluoroethyl, 1,2,2-trichloroethyl, 1,2,2-trifluoroethyl or pentafluoroethyl radical; or R$^4$ and R$^5$ together with the carbon atom to which they are attached form a cyclopropyl, cyclobutyl, cyclopentyl or cyclohexyl radical; R$^6$ and R$^7$, which may be the same or different, are each a hydrogen or halogen atom, an amino, carboxy, carbamoyl, cyano, 1-cyano-1-methylethyl or nitro radical, a methyl, ethyl, propyl, isopropyl, butyl, isobutyl, sec-butyl, tert-butyl, pentyl, isopentyl, hexyl, isohexyl, chloromethyl, dichloromethyl, trichloromethyl, fluoromethyl, difluoromethyl, trifluoromethyl, 2,2,2-trichloroethyl, 2,2,2-trifluoroethyl, 1,2,2-trichloroethyl, 1,2,2-trifluoroethyl, pentafluoroethyl, 2,2,3,3,3-pentafluoropropyl, 2,2-dichloro-3,3,3-trifluoropropyl, 4,4,4-trifluorobutyl, 5,5,5-trifluoropentyl or 6,6,6-trifluorohexyl radical, a mono- or di-(1-6C)-alkylcarbamoyl radical wherein the (1-6C)-alkyl is a methyl, ethyl, propyl, isopropyl, butyl, isobutyl, sec-butyl, tert-butyl, pentyl, isopentyl, hexyl or isohexyl radical, a mono- or di-(1-6C)halogenoalkylcarbamoyl radical wherein the (1-6C)halogenoalkyl is a chloromethyl, dichloromethyl, trichloromethyl, fluoromethyl, difluoromethyl, trifluoromethyl, 2,2,2-trichloroethyl, 2,2,2-trifluoroethyl, 1,2,2-trichloroethyl, 1,2,2-trifluoroethyl, pentafluoroethyl, 2,2,3,3,3-pentafluoropropyl, 2,2-dichloro-3,3,3-trifluoropropyl, 4,4,4-trifluorobutyl, 5,5,5-trifluoropentyl or 6,6,6-trifluorohexyl radical, or $R^6$ or $R^7$ is a radical of the formula —$COR^8$, —$SO_nR^8$ or —$OR^8$ wherein n is 0, 1 or 2 and $R^8$ is a methyl, ethyl, propyl, isopropyl, butyl, isobutyl, sec-butyl, tert-butyl, pentyl, isopentyl, hexyl, isohexyl, chloromethyl, dichloromethyl, trichloromethyl, fluoromethyl, difluoromethyl, trifluoromethyl, 2,2,2-trichloroethyl, 2,2,2-trifluoroethyl, 1,2,2-trichloroethyl, 1,2,2-trifluoroethyl, pentafluoroethyl, 2,2,3,3,3-pentafluoropropyl, 2,2-dichloro-3,3,3-trifluoropropyl, 4,4,4-trifluorobutyl, 5,5,5-trifluoropentyl or 6,6,6-trifluorohexyl radical, or $R^6$ or $R^7$ is a benzoyl radical optionally substituted by halogen; one of $R^9$ and $R^{10}$ is a hydrogen atom and the other is a methoxy, ethoxy, propoxy, isopropoxy, butoxy, pentyloxy or hexyloxy radical, or $R^9$ and $R^{10}$ together form an oxo radical, and the hydrochlorides, hydrobromides, sulphates, nitrates, phosphates and toluene-p-sulphonates, thereof.

3. A naphtho[2,1-b]furan derivative as claimed in claim 1 wherein $R^1$ is a 1H-1,2,4-triazol-1-yl or 4H-1,2,4-triazol-4-yl radical $R^2$ is hydrogen atom, $R^3$ is a hydrogen atom or a cyano, methyl, trifluoromethyl, 4-chlorophenyl or 1H-1,2,4-triazol-1-yl radical, $R^4$ and $R^5$ are both methyl or ethyl radicals, or $R^4$ and $R^5$, together with the carbon atom to which they are attached, form a cyclopentyl radical, $R^6$ and $R^7$, which may be the same or different, are each a hydrogen or bromo atom or a cyano, 4-chlorobenzoyl, nitro, amino, carbamoyl, carboxy, dimethylcarbamoyl, 2,2,2-trifluoroethylcarbamoyl or mesyl radical, and one of $R^9$ and $R^{10}$ is a hydrogen atom and the other is a hydroxy or ethoxy radical, or $R^9$ and $R^{10}$ together form an oxo radical.

4. A naphtho[2,1-b]furan derivative as claimed in claim 1 wherein $R^1$ is a 1H-1,2,4-triazol-1-yl radical, $R^2$ is a hydrogen atom, $R^3$ is a hydrogen atom or a 4-chlorophenyl or 1H-1,2,4-triazol-1-yl radical, $R^4$ and $R^5$ are both methyl radicals, $R^6$ is a hydrogen atom, $R^7$ is a hydrogen or bromo atom, or a cyano, 4-chlorobenzoyl, nitro, carbamoyl, 2,2,2-trifluoroethylcarbamoyl or mesyl radical, and $R^9$ and $R^{10}$ together form an oxo radical, or one is a hydrogen atom and the other is a hydroxy or ethoxy radical.

5. A naphtho[2,1-b]furan derivative as claimed in claim 1 which is 1,1-dimethyl-8-(1H-1,2,4-triazol-1-ylmethyl)-2(1H)-naphtho[2,1-b]furanone, 1,2-dihydro-1,1-dimethyl-2-oxo-8-(1H-1,2,4-triazol-1-ylmethyl)-naphtho[2,1-b]furan-7-carbonitrile, 1,2-dihydro-1, 1-diethyl-2-oxo-8-(1H-1,2,4-triazol-1-ylmethyl)naphtho[2,1-b]furan-7-carboxamide, or 1,2-dihydro-1,1-dimethyl-2-oxo-8-[di(1H-1,2,4-triazol-1-yl)methyl]-naphtho[2,1-b]furan-7-carbonitrile.

6. A pharmaceutical or veterinary composition which comprises an effective amount of a naphtho[2,1-b]furan derivative as claimed in claim 1 together with a pharmaceutically or veterinarily acceptable diluent or carrier.

7. A method for the treatment of steroid hormone dependent disease which comprises administering to a host in need of such treatment an effective amount of a naphtho[2,1-b]furan derivative as claimed in claim 1.

* * * * *